(12) United States Patent
Faubert et al.

(10) Patent No.: US 10,096,258 B2
(45) Date of Patent: Oct. 9, 2018

(54) PERCEPTUAL-COGNITIVE-MOTOR LEARNING SYSTEM AND METHOD

(71) Applicant: COGNISENS INC., Montréal, Québec (CA)

(72) Inventors: Jocelyn Faubert, Montréal (CA); Jean Castonguay, Vaudreuil-Dorion (CA)

(73) Assignee: COGNISENS INC., Quebec (CA)

(*) Notice: Subject to any disclaimer, the term of this patent is extended or adjusted under 35 U.S.C. 154(b) by 27 days.

(21) Appl. No.: 14/778,161

(22) PCT Filed: Mar. 18, 2014

(86) PCT No.: PCT/CA2014/000265
§ 371 (c)(1),
(2) Date: Sep. 18, 2015

(87) PCT Pub. No.: WO2014/146192
PCT Pub. Date: Sep. 25, 2014

(65) Prior Publication Data
US 2016/0351069 A1    Dec. 1, 2016

Related U.S. Application Data

(60) Provisional application No. 61/802,758, filed on Mar. 18, 2013.

(51) Int. Cl.
*G09B 19/00* (2006.01)
*A61B 5/16* (2006.01)
*G06F 19/00* (2018.01)

(52) U.S. Cl.
CPC ............... *G09B 19/00* (2013.01); *A61B 5/16* (2013.01); *G06F 19/3481* (2013.01); *G09B 19/0038* (2013.01)

(58) Field of Classification Search
CPC ... A61B 5/16; G06F 19/3481; G09B 19/0038; G09B 19/00
See application file for complete search history.

(56) References Cited

U.S. PATENT DOCUMENTS 6,632,174 B1 * 10/2003 Breznitz ............... A61B 5/16
434/236
2003/0013981 A1 * 1/2003 Gevins ............... A61B 5/0484
600/544

(Continued)

FOREIGN PATENT DOCUMENTS

EP    0 880 380 A1    12/1998
EP    2 676 256 A1    12/2013

(Continued)

OTHER PUBLICATIONS

Faubert, et al., "Perceptual-Cognitive Training of Athletes," Journal of Clinical Sport Psychology, 2012, 6, 85-102.

(Continued)

*Primary Examiner* — Nathan Hillery
(74) *Attorney, Agent, or Firm* — Muirhead and Saturnelli, LLC (57) ABSTRACT

The present disclosure relates to a perceptual-cognitive-motor learning system. The system includes an apparatus for evaluating or improving perceptual-cognitive abilities of a subject during a training sequence. The apparatus includes a display configured to provide to the subject a visual contact with an environment. The system also has a training sequence controller configured to consolidate results of first successive tests made using a single spatial zone formed by the environment, segment the into a plurality of spatial zones, and consolidate results of second successive tests made using the plurality of spatial zones. Methods for evaluating or improving perceptual-cognitive abilities of a subject are also disclosed.

13 Claims, 8 Drawing Sheets

(56) References Cited

U.S. PATENT DOCUMENTS

| | | | |
|---|---|---|---|
| 2003/0059759 A1* | 3/2003 | Calhoun | G06F 19/3418 |
| | | | 434/322 |
| 2003/0077556 A1* | 4/2003 | French | A61B 5/1113 |
| | | | 434/258 |
| 2004/0002046 A1 | 1/2004 | Cantor | |
| 2004/0049124 A1* | 3/2004 | Kullok | A61B 5/16 |
| | | | 600/558 |
| 2004/0230549 A1* | 11/2004 | Freer | A61B 5/0482 |
| | | | 706/61 |
| 2005/0216243 A1* | 9/2005 | Graham | G06F 19/3437 |
| | | | 703/11 |
| 2006/0003298 A1 | 1/2006 | Greenshpan et al. | |
| 2011/0213197 A1 | 9/2011 | Robertson et al. | |
| 2011/0298706 A1 | 12/2011 | Mann | |
| 2011/0300522 A1* | 12/2011 | Faubert | A61B 5/16 |
| | | | 434/236 |
| 2012/0090446 A1* | 4/2012 | Moreno | G09B 15/00 |
| | | | 84/470 R |
| 2013/0046206 A1* | 2/2013 | Preminger | G09B 7/02 |
| | | | 600/595 |
| 2013/0266918 A1* | 10/2013 | Tinjust | A63B 69/0053 |
| | | | 434/247 |
| 2016/0155355 A1* | 6/2016 | Merzenich | A63F 13/80 |
| | | | 434/236 |

FOREIGN PATENT DOCUMENTS

| | | |
|---|---|---|
| JP | 2006-288916 A | 10/2006 |
| JP | 2010-104475 A | 5/2010 |
| WO | WO 2004/006747 A2 | 1/2004 |
| WO | WO 2010/037222 A1 | 4/2010 |
| WO | WO 2011/048524 A1 | 4/2011 |
| WO | WO 2012/148524 A1 | 11/2012 |
| WO | WO 2013/123587 A1 | 8/2013 |

OTHER PUBLICATIONS

Legault, et al., Healthy older observers cannot use biological-motion point-light information efficiently within 4m of themselves, i-Perception (2012), vol. 3, pp. 1-8.

Goodale, « Transforming vision into action », Vision Research 51 (2011) 1567-1587.

* cited by examiner

PERCEPTUAL-COGNITIVE-MOTOR LEARNING SYSTEM AND METHOD

TECHNICAL FIELD

The present disclosure relates to the field of perceptual-cognitive training. More specifically, the present disclosure relates to a perceptual-cognitive-motor learning system and method.

BACKGROUND

In our daily activities, we constantly interact with our environment. This environment is dynamic and requires the integration of various objects, motions, speeds, locations, etc. As a result, the brain's executive functions are constantly managing myriads of stimuli. Risk of information overload is present in many real-life situations. Ability to deal quickly with unpredictability of stimuli in time sensitive situations is a real-life need in the office, in sports, in school, and in crisis management situations.

Attention and focus applied to strategic inputs can make a difference between winning and losing in sports activities, in learning new skills, in facing dangerous situations, and leading a successful professional career. Attention and focus, especially in stressful situations, enable filtering and prioritizing of data while disregarding irrelevant distractors.

In the case of elderly people or persons with certain disabilities, deficits in attention and focus can cause serious problems in routine activities. For instance, travelling through a crowd while avoiding collisions and maintaining orientation and good motor control requires fluent and continuous perceptual-cognitive processing. It is well documented that effects of healthy aging can influence perceptual cognitive processes.

Loss of attention and impaired impulse control can be a severe problem for children with attention deficit disorder, with or without hyperactivity, and for autistic children.

The need to improve attention and focus is therefore present in a broad range of individuals. This need is especially present in persons having learning disabilities or with degrading cognitive functions. This need is also present in high end athletes who need to "read the game" while following the trajectory of a ball, and in members of many professions who need deal with masses of information.

Therefore, there is a need for solutions that help improving cognitive functions, whether for children having learning disabilities, aging persons, athletes or professionals operating in stressful environments.

SUMMARY

According to the present disclosure, there is provided a perceptual-cognitive-motor learning system. The system comprises an apparatus for evaluating or improving perceptual-cognitive abilities of a subject during successive tests. The apparatus includes a display configured to provide to the subject a visual contact with an environment. The system also comprises means for consolidating results of first successive tests made using a single spatial zone formed by the environment, means for segmenting the environment into a plurality of spatial zones, and means for consolidating results of second successive tests made using the plurality of spatial zones.

According to the present disclosure, there is also provided a perceptual-cognitive-motor learning system. The system comprises an apparatus for evaluating or improving perceptual-cognitive abilities of a subject during successive tests. The apparatus includes a display configured to provide to the subject a visual contact with an environment. The system also comprises a training sequence controller. The training sequence controller is configured to consolidate results of first successive tests made using a single spatial zone formed by the environment, segment the environment into a plurality of spatial zones, and consolidate results of second successive tests made using the plurality of spatial zones.

The present disclosure also relates to a method for evaluating or improving perceptual-cognitive abilities of a subject. The subject is submitted to a training sequence. The training sequence includes a plurality of successive tests presented to the subject in an environment. Results of first successive tests made using a single spatial zone formed by the environment are consolidated. The environment is segmented into a plurality of spatial zones. Results of second successive tests made using the plurality of spatial zones are consolidated.

The foregoing and other features will become more apparent upon reading of the following non-restrictive description of illustrative embodiments thereof, given by way of example only with reference to the accompanying drawings.

BRIEF DESCRIPTION OF THE DRAWINGS

Embodiments of the disclosure will be described by way of example only with reference to the accompanying drawings, in which.

DETAILED DESCRIPTION

Like numerals represent like features on the various drawings.

Various aspects of the present disclosure generally address one or more of the problems of improving cognitive functions.

The following description discloses a non-limitative, illustrative embodiment of the NeuroTracker "Perceptual-Cognitive-Motor" Learning System (NT-LS). More specifically, the three (3) following features of the NT-LS are described:

1—A NeuroTracker (NT) motor add-on system where motor add-ons are made under very specific conditions for optimized learning.

2—A "Self-Paced" system and method for rapidly assessing individual thresholds.

3—A new general concept of the NT-LS is introduced. More specifically, there is demonstrated how the NT-LS can be scaled for progressively increasing field relevance of the training for sports and for any emergency decision-action taking and/or crisis management situation.

1—the NT-Motor Add-on System

Sports performance (also true for common life situations like navigation in crowds) involves the capacity to rapidly process complex movement over large areas and in a three-dimensional (3D) environment, including sudden changes in directions and collisions and at the same time attend to multiple key elements in the scene, i.e. in the environment. Information from the scene is integrated with specific motor demands in the sport or for real-life demands like navigating in crowds. In other words, human beings perceive and understand what is happening in their environment while at the same time interacting with it physically, with specific actions. There is evidence for specialized visual brain systems where some pathways are responsible for perception and some for action. Although these specialized visual brain systems for perception and for action comprise distinctive elements they are ultimately combined.

It is also believed with evidence from science that the vision for perception system is more complex and more recent on the evolutionary scale than the vision for action system.

The ultimate transfer and closure of the sensory-perceptual-cognitive-motor loop involves a way to combine all of the above abilities in training. It is also desirable to isolate and consolidate these abilities and then combine them on training. The present disclosure proposes to train on the NT-LS to build this consolidation, as it involves the more complex perception visual system and, once consolidated, close the visual-perceptual-cognitive-motor loop with motor tasks integrated with the NT.

1a) Evidence for Requiring the Consolidation Process

Figure 1:
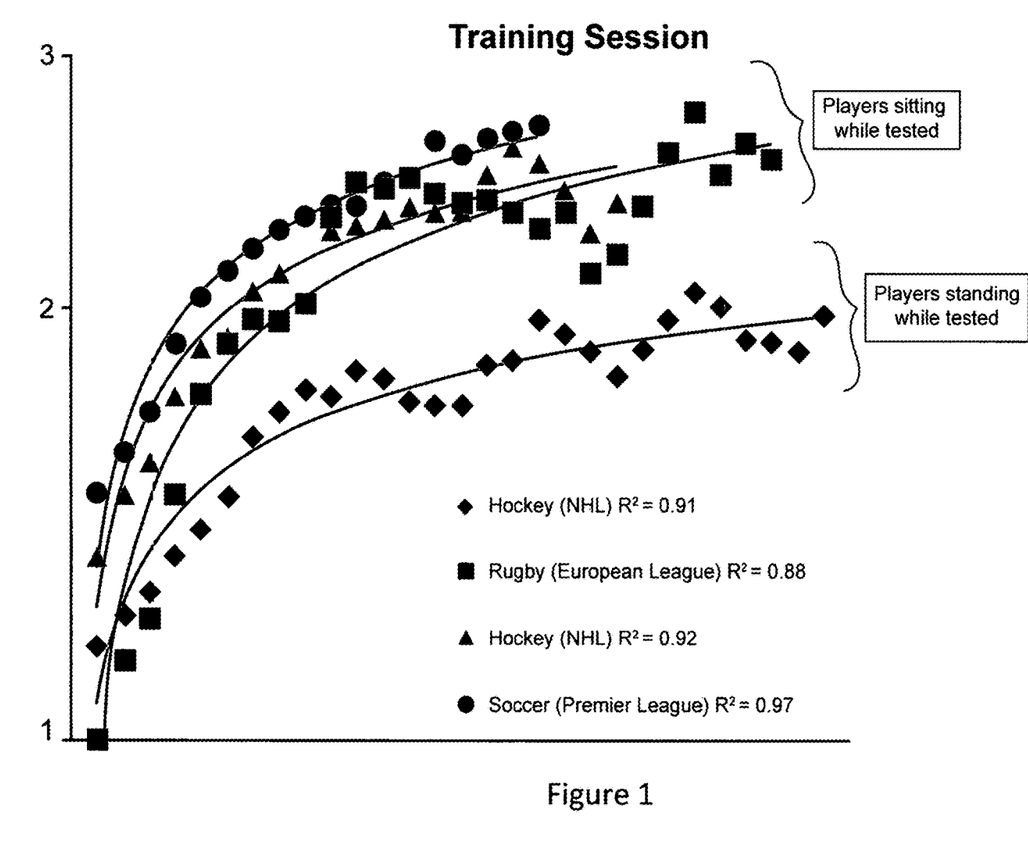
FIG. 1 is a graph showing learning curves of athletes subjected to a demanding training regime.
Figure 2:
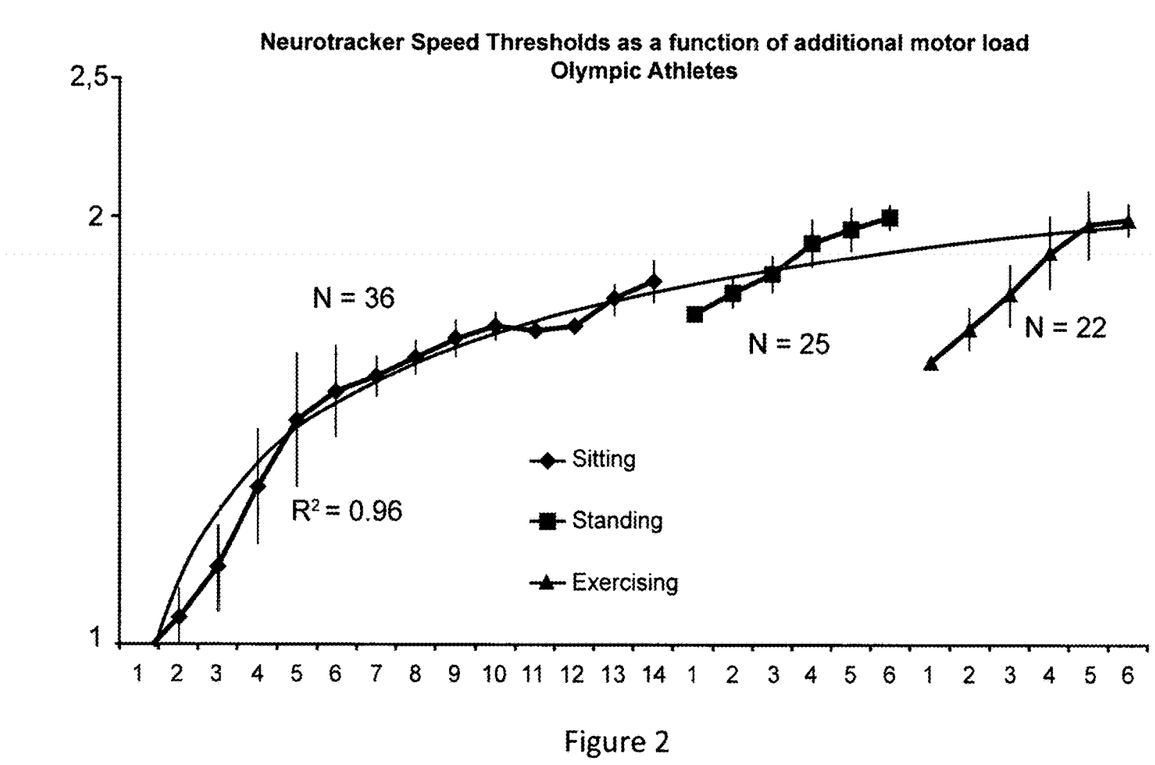
FIG. 2 is a graph showing learning curves of athletes subjected to a demanding training regime when using a perceptual-cognitive-motor system.

An initial study has demonstrated that added motor demand at the beginning of a demanding perceptual-cognitive training regime can be detrimental to the acquisition phase. FIG. 1 is a graph showing learning curves of athletes subjected to a demanding training regime. The graph demonstrates that added motor demand at the beginning of a demanding perceptual-cognitive training regime can be detrimental to a subject's acquisition phase. What was found from training of high-level professional athletes was that if the players learned a task standing up from start, their levels of performance were lower and their learning curves were shallower. To understand this further, the initial study was followed with an experiment looking at the transferability of training when carrying out consolidation first followed by adding motor load on top of the training. What it is meant by transferability is that the benefit of learning in one condition is maintained in another condition. The results of this study are shown in FIG. 2, which is a graph showing learning curves of athletes subjected to a demanding training regime when using a perceptual-cognitive-motor system. This graph shows that, following consolidation when the subject is sitting, very little loss in performance is observed when standing, and that although there is an initial large drop in a condition of exercising, athletes quickly regain their speed processing capacities and get back on the usual learning curve of the "sitting down" position. The first 14 training sessions show the usual progression of speed of processing ability when sitting down, followed by the next six sessions with the athlete standing up, followed by the last six training sessions with the athlete sitting on a Bosu™ balance ball in a position that makes it difficult to maintain balance. As can be observed from FIG. 2, after consolidation (sitting), there is very little loss in performance when standing, which shows evidence of transfer. Although there is an initial large drop in the third condition (exercising; sitting on Bosu™ ball) the athletes quickly regain their speed processing capacities and get back on the usual learning curve of the "sitting down" position.

1b) Closing the Loop

This section describes a method and system for closing of the visual-perceptual-cognitive-motor loop for optimal performance and combining of the NT technology with an objective measure of visual-motor performance system. A subject is submitted to a training sequence according to the following scheme:

$[n_1(CORE); n_2(CORE+MOTORa); n_3(CORE+MOTORb)]$.

The training sequence comprises $n_1$ repetitions of a core exercise, followed by $n_2$ repetitions of the core exercise performed in conjunction with a first (usually light) motor demand, and followed by $n_3$ repetitions of the core exercise performed in conjunction with a second (usually heavier) motor demand. Generally, the values of $n_1$, $n_2$ and $n_3$ are non-negative integers.

As a non-limitative example, the training can be performed using an apparatus as described in PCT patent application No PCT/CA2009/001379 filed on Sep. 29, 2009 in the name of Faubert et al., and published on Apr. 8, 2010 under No WO 2010/037222 A1 (hereinafter "Faubert'222"), the full content of which being herein incorporated by reference.

Figure 3:
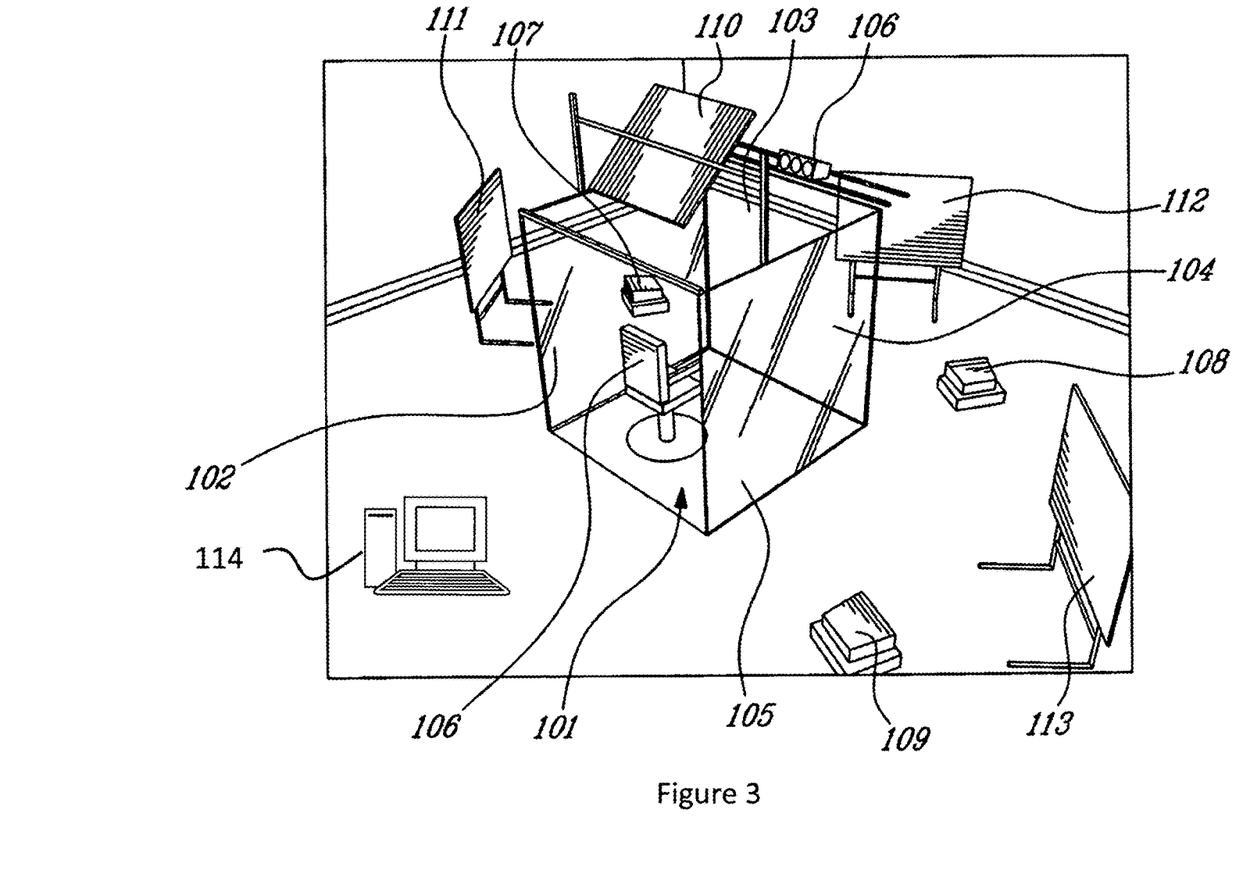
FIG. 3 is a perspective view of an example of full immersive virtual environment.

The apparatus introduced in Fauber'222 can be used for evaluating or improving perceptual-cognitive abilities of a subject. The apparatus comprises a display of virtual objects moving a given 3D environment during successive tests. FIG. 3 is a perspective view of an example of full immersive virtual environment. More specifically, the display comprises a fully immersive virtual environment (FIVE) room 101, for example a CAVE™ Automatic Virtual Environment, from Fakespace Systems, in which the subject is fully immersed in the given 3D environment and the stimuli are presented. The fully immersive virtual environment room 101 has a size of, for example, 8×8×8 feet and comprises four (4) projection surfaces (three walls 102, 103 and 104, and a floor 105). The display shows stereoscopic images on the four (4) projection surfaces (the three walls 102, 103 and 104, and floor 105) to form the given 3D environment in which virtual objects are presented. The display comprises, for that purpose, projectors 106, 107, 108 and 109 and associated planar reflectors 110, 111, 112 and 113, respectively to project and display the images on the four (4) projection surfaces (the three walls 102, 103 and 104 and floor 105) under the control of a computer 114 acting as a display controller. Interconnections between the computer 114 and other elements of the FIVE room 101 are not shown for simplicity purposes. The computer 114 may be linked to the various projectors 106, 107, 108 and 109 and to other networked elements using any well-known connection methods.

The display of the apparatus for evaluating or improving perceptual-cognitive abilities of a subject also comprises a shutter visual implement, for example under the form of liquid crystal shutter stereoscopic goggles (not shown) from Stereographics, San Rafael, Calif., to enable the subject's 3D stereoscopic perception, more particularly to enable the subject to perceive in 3D the virtual object, the positions of the virtual objects and the 3D environment. Stereoscopic images are rendered with a refresh rate of 48 Hz and the goggles are shuttered at 96 Hz to deliver 48 images per second to the subject's right and left eyes. The display further comprises a positional sensor, for example under the form of a magnetic detector, for example a Flock of Birds™, from Ascension technology corp., Burlington, Vt., mounted to the goggles in order to track a position of the subject's head. The computer 114 controls the display to correct in real-time a visual perspective relative to the tracked subject's head position. The display controller (for example a "Silicon graphics 540" computer) generates the stimuli and records the subject's responses.

An ophthalmologic chair 106 positioned substantially in a central position of the FIVE room 101 is provided to sit the subject.

The apparatus of Faubert'222 can therefore be used in support of a method for evaluating or improving perceptual-cognitive abilities of a subject. In summary, this apparatus comprises a display of virtual objects moving in a given 3D environment during successive tests, with the subject in visual contact with the virtual objects moving in the 3D environment. The computer 14 controls the projectors 106, 107, 108 and 109 to change a speed of movement of the virtual objects in the 3D environment. During each test, the subject tracks a subset of the moving virtual objects and, after the test, the subject identifies the tracked objects. It should be kept in mind that the training and other functions disclosed herein may alternatively be performed using any other suitable device.

CORE represents a test comprising a 6-8 minutes testing sequence using the apparatus as described in Faubert'222.

CORE+MOTORa represents a test comprising a low-level simple motor load add-on to the CORE test. This can be a standing up position of the subject but could also be bicycling, or just holding onto a rail or a treadmill with ice or rolling skates. This means that the CORE+MOTORa test is calibrated so that there is no efferent signal (brain command of movement) from the brain to move limbs in a meaningful pattern such as running, skating or intercepting a ball.

CORE+MOTORb represents a test going one level higher, the MOTORb load thus being heavier than the MOTORa load. During a CORE+MOTORb test, the subject is asked to merge the CORE with a specific motor demand that is adapted to a given real-life situation, for example a sport, operation of a machine or of a vehicle, a hazardous situation, or any other similar purpose. There is no a priori limit to the type of situation that can be represented during the CORE+MOTORb test.

A training sequence controller, integrated in the computer 114 or in a separate computer (not shown), controls the apparatus as described in Faubert'222 in order to perform the training sequence. Sensors may also be connected to the subject and the training sequence controller for monitoring the movements of the subject during each test, in particular movements related to MOTORa add-ons and MOTORb motion.

According to an example of implementation taking into consideration available, gathered scientific data, the following training sequence is performed under the control of the training sequence controller:

[$n_1$(CORE);    $n_2$(CORE+MOTORa);    $n_3$(CORE+MOTORb)].

wherein:
$n_1$=10 to 15 repetitions;
$n_3$=6 repetitions; and
$n_3$=6 repetitions.

More specifically, the training sequence controller controls the apparatus as described in Faubert'222 to perform, in sequence, a series of 10 to 15 CORE tests, a series of 6 CORE+MOTORa tests, and a series of 6 CORE+MOTORb tests. After each test, the computer 114 collects the responses of the subject in relation to the identification of the tracked virtual objects (for example spheres) through a response interface, for example a keyboard with a display of the computer 114, for further analysis of these responses, for example an analysis as described in the aforementioned Faubert'222, potentially in combination with an analysis of the movements of the subject during the tests in case of CORE+MOTORa and CORE+MOTORb tests to determine the evolution of the subject. Such analysis of the training sequence can be limited to the tracing of graphs or can be much more complex depending on the requirements of the intended application.

Using the above example of implementation ($n_1$=10 to 15 repetitions, $n_3$=6 repetitions, and $n_3$=6 repetitions), it is possible to increase motor skill with a method based on scientific data and adapt it to any sport or rehabilitation training. For instance, it is easy to imagine someone who suffered a stroke and had some difficulty walking, to be gradually rehabilitated using such a method where MOTORb becomes walking on a treadmill. The following are also some examples of MOTORb:

Rugby: Catching a lateral pass;
Hockey: Receiving a pass and shooting puck, or stopping a puck for a goalie;
Soccer: receiving and redirecting a ball;
Etc.

2—"Self-Paced" System and Method

The self-paced system and method address some issues by the users (subjects) of the NT-LS system. These issues comprise:

A technique for getting speed thresholds more rapidly than the usual 6-8 minutes CORE test in situations such as testing at combines (recruitment of junior drafts), rapid throughput, etc.

A technique to keep the subject active during the test even if the subject lost tracking of the virtual objects (see the apparatus as described in Faubert'222). The classic CORE test is set-up so that if the subject loses one or more of the tracked objects, there was no chance of reset or recall during the test that lasts 6-8 seconds. The subject waits until the end, gives the response and starts again.

The self-paced system and method resolves this issue by allowing the subject to stay active and do several things on his own and online to the dynamic visual scene. Also, there are two versions of the self-paced system and method, the training mode and the assessment (measurement) mode although these two versions are not mutually exclusive.

Figure 4:
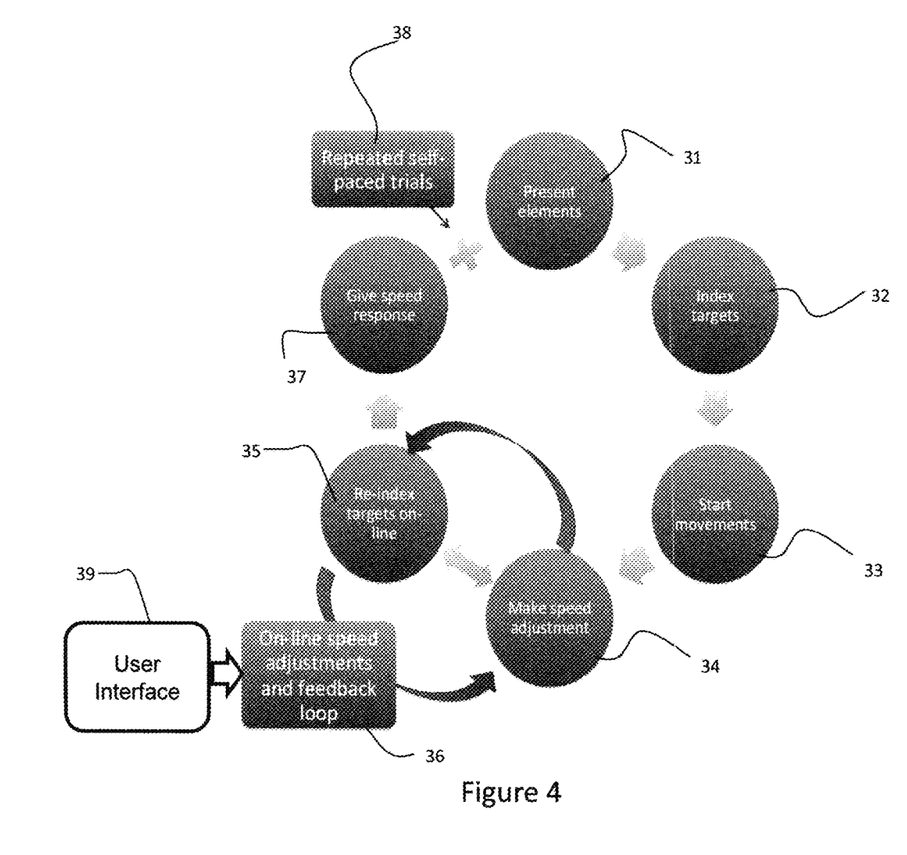
FIG. 4 is a schematic diagram illustrating a training self-paced mode.

Referring to FIG. 4, which is a schematic diagram illustrating a training self-paced mode, a typical CORE test works the following way. As directed by the training sequence controller, the display of the apparatus as described in Faubert'222 presents to the subject a number of virtual objects (typically 8 spheres) as seen in block 31 of FIG. 4. Then the training sequence controller indexes a subset (usually 4 spheres representing the target objects) by changing color or flashing, etc. (block 32 in FIG. 4). Then the objects return to their original condition. The training sequence controller then starts movement of the objects in the 3D environment as shown in block 33 of FIG. 4. Once the movement of the objects starts then the subject can use a user interface 39, which is operatively connected to the computer 114, to make the following adjustments:

Training Self-Paced Mode:

In this case the subject can issue commands directed to the training sequence controller via the user interface 39 to perform the following actions:

Managing the speed, i.e. make the virtual objects in the dynamic 3D environment move faster or slower at will by pressing buttons or giving certain commands, for example vocal commands to a remote module (not shown), or by physical gesture detected by a motion capture device (not shown) for example by moving hands up and down or spreading apart or closing together the hands. The remote module or motion capture device is connected to the computer 114 that incorporates the training sequence controller (blocks 34 and 36 of FIG. 4).

Allowing for a reset, recall or re-indexing of the target objects at any time during tracking and for any desired length up to a certain limit (block 35 of FIG. 4).

At any time during the test, the subject can indicate by depressing a button of the remote module or through any other command, that a given speed of the virtual objects is the correct tracking speed (block 37 of FIG. 4). More specifically, when the subject feels the speed is correct and he can maintain the tracking of the target objects at that speed, the subject then presses a button of the remote module and the selected speed is automatically received and recorded by the computer 114. Alternatively, or in addition, electroencephalogram (EEG) sensors (not shown) operably connected to the computer 114 may detect brain waves of the subject. The computer 114 may analyze the brain waves to determine when the subject is losing focus and is no longer able to maintain the tracking of the target objects. The computer 114 may for example determine that a correct speed is a previous (lower) speed before the loss of focus detection. When the subject presses the button, or based on the detection from the EEG sensors, the targets are refreshed and when the button is released, or when the EEG sensors show that brain waves refocus, the indexing disappears while the movement continues. This refresh can be repeated any number of times (block 38 of FIG. 4). That is, one subject can train for as long as desired by providing feedback commands to the self-paced system. The subject can continue using the method without resetting or may have as many rests as desired.

Depending on the type of adjustment made by the subject in the training self-pace mode, the user interface 39 may comprise one or more buttons, a microphone connected to a speech detector (not shown), a motion capture device, a keyboard, a pedalboard, of any other man-machine interface.

Figure 5:
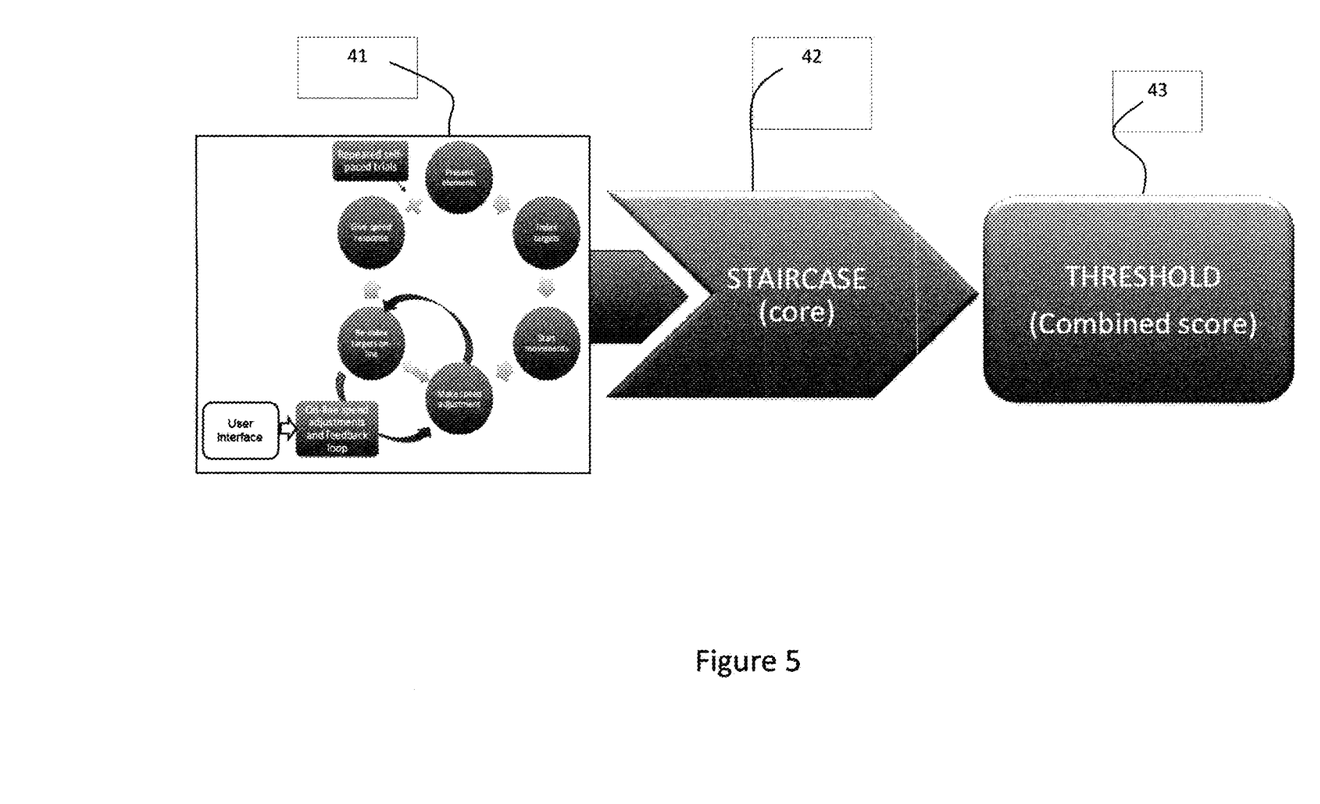
FIG. 5 is a schematic diagram illustrating an assessment self-paced mode incorporating the training self-paced mode of FIG. 4 and an additional use of a staircase (up and down) variation of speeds.

Assessment Self-Paced Mode:

FIG. 5 is a schematic diagram illustrating an assessment self-paced mode incorporating the training self-paced mode of FIG. 4 and an additional use of a staircase (up and down) variation of speeds. The assessment self-paced mode incorporates the operations of the training self-paced mode (block 41 of FIG. 5) except that it has the following additional operation (block 42 of FIG. 5):

When a pre-set number of speed adjustments has been terminated in block 41, the training sequence controller automatically performs a preset number of tests using a shortened staircase (up and down) variation of speeds such as the one used for the CORE test and as described in the apparatus of Faubert'222. This procedure ensures that the subjective speed adjustments made by the subject, or made on the basis of EEG sensor detections, truly correspond to speed threshold values as objectively determined (block 42 of FIG. 5).

The "self-paced" system and method have the following characteristics:
1) They can be very fast;
2) They are very flexible for various training times;
3) They permit the subject to stay in the "zone" of maximum trainability where stands the right level of difficulty for any subject at any given time; and
4) They help in developing the subject's ability to recognize their own internal mental state and respond to it by making appropriate adjustments.

The self-paced system and method not only assess speed thresholds (block 43 of FIG. 5) by calculating the given responses and the results of the staircase variation of speed (block 42 of FIG. 5) when the assessment self-paced mode is used, but it also allows the computer 114 to perform a number of measures, useful in determining the speed thresholds, while the subject is participating such as:

a) A number of target recalls (number of repetitions of the self-paced trials);
b) A time of each recall (repetition rate of the self-paced trials); and
c) Speed values during the self-paced recalls.

Figure 6:
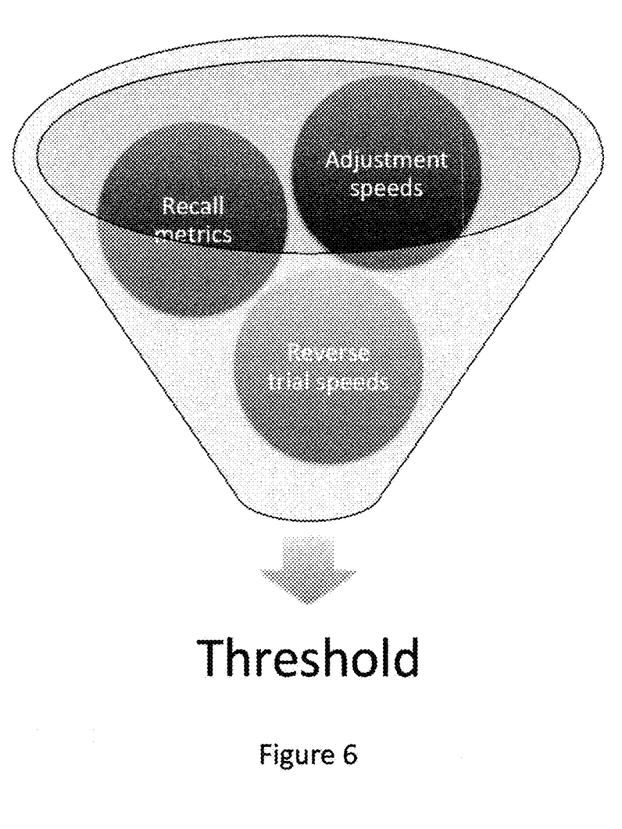
FIG. 6 is a schematic diagram illustrating the use of a number of measures to determine speed thresholds.

This is illustrated in FIG. 6, which is a schematic diagram illustrating the use of a number of measures to determine speed thresholds, and can be used to develop response profiles and learning profiles for each subject.

The efficiency of the self-paced assessment mode to determine whether this mode can generate similar results as the CORE test for the initial "consolidation" stage has been tested. During the test, the subjects used the assessment self-paced mode (2 adjustments and 6 staircase trials) for the first 4 training sessions, followed by a regular CORE assessment measure on the 5th session followed by another 4 assessment self-paced sessions followed by a CORE session as the 10th session etc. It was found that the 5th, 10th and 15th CORE session scores followed well with the self-paced score indicating that the assessment self-paced mode can be used to obtain similar results but with much shorter training times i.e. 3 minutes versus 6-8 minutes with the CORE test.

3—General Concept of the NT-LS

The following section presents a general concept of the NT-LS. The NT-LS incorporates a protocol to establish a learning scheme adapted to any situation that requires rapid decisions when multiple sources of information are managed. As expressed in the above description of motor add-ons, consolidation is performed prior to adding functional loads such as different levels of a perceptual-motor skill. The same is true for adding other cognitive loads such as scene specificity and contextual information that evolves towards play-book examples in sports or evacuation drills in crisis management situations such as emergency evacuations. Scene specificity and contextual information may relate to stadiums, buildings, train and subway stations, airports, planes, boats, hospitals, schools, or any physical space where many events and/or decisions occur simultaneously. The NT-LS enables building the rapid-decision making ability of individuals that are confronted with important decisions under time pressure.

Figure 7:
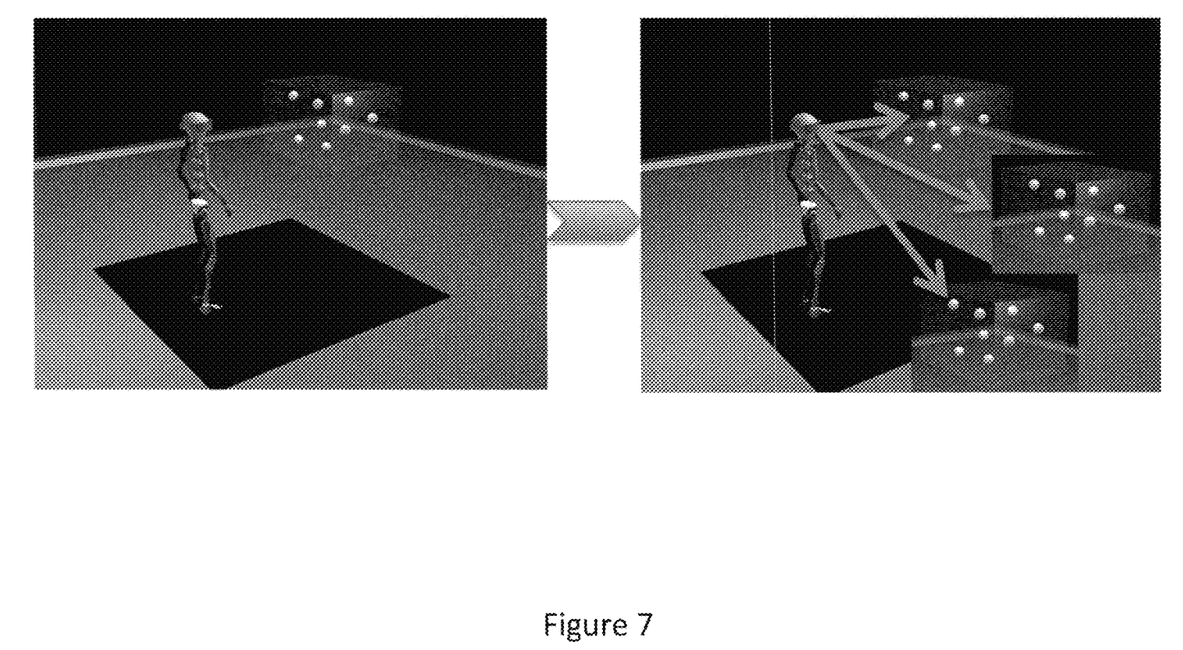
FIG. 7 illustrates segmentation of a scene into a plurality of spatial zones.

The NT-LS uses the speed threshold consolidation process described hereinabove and builds on increasing cognitive loads while maintaining the speed threshold protocols. In the following paragraphs, for illustration purposes, American Football will be used as a non-limitative example. In this example, a quarterback needs to ultimately process different target zones that include running backs, wide receivers, tight-ends, and other players to make a good pass play. The quarterback first processes the near zone and then expands his ability to track multiple elements by zone. The NT-LS may operate in the following manner:

Phase 1: Build the subject's ability to process a segmented scene distribution. Reference is now made to FIG. 7, which illustrates segmentation of a scene into a plurality of spatial zones. The left-hand side of FIG. 7 shows a 3D scene. The right-hand side of FIG. 7 shows the same 3D scene following segmentation into three (3) spatial zones. In the example of FIG. 7, the spatial zones consist of separate volumetric (3D) spaces showing moving objects. Segmentation can be made over a smaller or larger number of spatial zones. The following operations are performed by the training sequence controller:

Consolidation over 12 to 15 training sessions. The consolidation may use the CORE or use an assessment self-paced mode.

Separation (segmentation) of the tracking into two spatial zones. As an example, instead of having an initial unique zone to train, a number of elements to be tracked may be divided so that each distinct spatial zone contains some of the elements, including a few targets, as shown on the right-hand side of FIG. 7.

New consolidation back to initial reference values (e.g. geometrical mean speed of last three (3) values of the consolidation).

Further split (segmentation) of the tracking, into a larger number of spatial zones that are further split, with predefined targets and distracter elements that are suited to the situation.

Phase 2: Build the subject's capacity to process different viewing perspectives. Once the subject has developed the capacity to process multiple target zone NT ability, the training sequence controller introduces different visual specific perspectives in a manner analogous to the above mentioned operations. These perspectives may comprise:

Viewing angle, for example viewing perspective from the quarterback, from the receiver, and the like.

Viewing angle from horizontal to a more angular perspective, for example simulating a football player moving from a crouching to a standing position.

Phase 3: Building ecologically valid environments. The following operations are performed by the training sequence controller:

Once Phases 1 & 2 have been completed, the training sequence controller can move on to more realistic virtual environments such as using virtual stadiums, avatars with gradual levels using the same strategies.

The training sequence controller may increase the loads during training by introducing backgrounds, situational contexts, auditory noise and sounds, and so on to build towards specificity of training while measuring NT speed thresholds throughout.

Of course, this approach can be adapted, and evolve as a consequence of client.

3a) Specific Avatar NT Animation

When using avatars, the training sequence controller animates them in a specific way to allow for NT speed threshold measurements. For instance, random biological movements of the avatars may be implemented versus action specific movements for some target avatars. For example, non-target avatars may be composed of non-specific biological movement noise (for a description of biological motion noise, see Legault, I., Troje, N. F. & Faubert, J. (2012), *Healthy older observers cannot use biological-motion point-light information efficiently within 4 m of themselves*, i-Perception, 3(2), 104-111, the disclosure of which being incorporated by reference herein). However, the target avatars may have specific actions meaningful for the simulated play, for example turning in one direction, running forward or backward, and the like. Speed manipulation follows the usual NT rules in that speed increases when decisions are good after a temporal exposure or decreases if a mistake is made. Implementation of such manipulations of avatars or biological motion conditions is believed to be original in the context of perceptual-cognitive training.

3b) Different Cognitive Tasks

Two (2) elements for the development of the NT-LS from general to specific have been presented hereinabove. These elements include a) a spatial localisation (e.g. separating the volume space into sub regions with high-salience values for a task), and b) a change of specific attributes of the targets and distracters so that they evolve from, for example, a general sphere nature to a specific characteristic such as, for example, a human avatar.

While these elements have so far been described using examples involving human avatars, other examples may involve moving vehicles, for purposes of training a subject in taking appropriate decisions for collision avoidance in the presence of simulated moving traffic. Of course, moving objects and avatars may be used in combination. For example, traffic simulation may involve moving vehicles and pedestrians.

Figure 8:
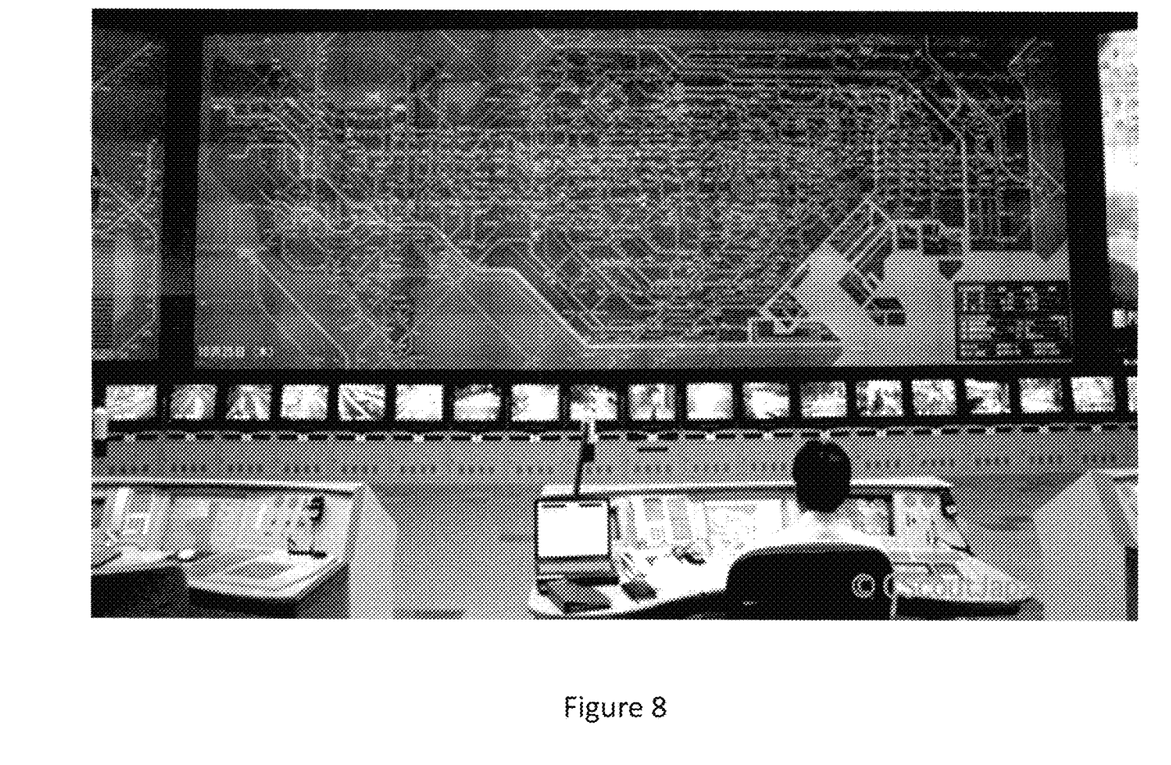
FIG. 8 illustrates a traffic control room in Tokyo, forming a segmented scene distribution.

A $3^{rd}$ component that may be introduced is a nature of the cognitive demand. For instance, instead of tracking targets among distracters in a given region, the subject may be asked to perform a mathematical task because this is what is required in that region versus a motion tracking task in another. To this end, a variant of the concept of segmented scene, which was introduced hereinabove, is illustrated by FIG. 8, which illustrates a traffic control room in Tokyo, forming a segmented scene distribution. FIG. 8 shows distinct motion components in some area of an operator's visual field (video monitors) and a possible colour code assessment in a large upper panel. The operator is required to process these various motion components, which are spatially distributed within his visual field. The training sequence controller may be used primarily for training the operator in moving target tracking for objects in his lower visual field. Concurrently, an analysis of the upper visual field may be performed to identify some colors or some patterns using pattern matching.

The NT-LS can thus be made to evolve from a general learning system to a more specific learning system. Each level of specificity training may involve using the same basic principles of the NeuroTracker, including for example speed thresholds by homing in on the fastest speeds at which each task can be performed.

From General to Specific Training

In conclusion, the NT-LS is adaptable from general training of basic properties for managing complex dynamic scenes under pressure to increasing specificity training by changing three (3) properties of the scene components:

The spatial configuration, going from a large general volume space to subdivisions of this space emphasizing particularly important zones for specific tasks.

The elements that are being processed or tracked, changing from, for example, a general sphere nature to a more specific characteristic of the image element such as, for example, avatars for crowd movements, moving objects, moving vehicles in traffic, and the like.

The third element that may be varied from general to specific is an actual cognitive task being performed in a specific 3D zone. In some cases, the task includes target tracking. In other cases, the task may require color code identification, a mathematical task, and the like.

Those of ordinary skill in the art will realize that the description of the perceptual-cognitive-motor system and method are illustrative only and are not intended to be in any way limiting. Other embodiments will readily suggest themselves to such persons with ordinary skill in the art having the benefit of the present disclosure. Furthermore, the disclosed perceptual-cognitive-motor system and method may be customized to offer valuable solutions to existing needs and problems of improving cognitive functions.

In the interest of clarity, not all of the routine features of the implementations of the perceptual-cognitive-motor system and method are shown and described. It will, of course, be appreciated that in the development of any such actual implementation of the perceptual-cognitive-motor system and method, numerous implementation-specific decisions may need to be made in order to achieve the developer's specific goals, such as compliance with application-, system-, and business-related constraints, and that these specific goals will vary from one implementation to another and from one developer to another. Moreover, it will be appreciated that a development effort might be complex and time-consuming, but would nevertheless be a routine undertaking of engineering for those of ordinary skill in the field of perceptual-cognitive training having the benefit of the present disclosure.

In accordance with the present disclosure, the components, process operations, and/or data structures described herein may be implemented using various types of operating systems, computing platforms, network devices, computer programs, and/or general purpose machines. In addition, those of ordinary skill in the art will recognize that devices of a less general purpose nature, such as hardwired devices, field programmable gate arrays (FPGAs), application specific integrated circuits (ASICs), or the like, may also be used. Where a method comprising a series of process operations is implemented by a computer or a machine and those process operations may be stored as a series of instructions readable by the machine, they may be stored on a tangible medium.

Systems and modules described herein may comprise software, firmware, hardware, or any combination(s) of software, firmware, or hardware suitable for the purposes described herein. Software and other modules may reside on servers, workstations, personal computers, computerized tablets, personal digital assistants (PDA), and other devices suitable for the purposes described herein. Software and other modules may be accessible via local memory, via a network, via a browser or other application or via other means suitable for the purposes described herein. Data structures described herein may comprise computer files, variables, programming arrays, programming structures, or any electronic information storage schemes or methods, or any combinations thereof, suitable for the purposes described herein.

Although the present disclosure has been described hereinabove by way of non-restrictive, illustrative embodiments thereof, these embodiments may be modified at will within the scope of the appended claims without departing from the spirit and nature of the present disclosure.

What is claimed is:

1. A perceptual-cognitive-motor learning system comprising:
    an apparatus for evaluating or improving perceptual-cognitive abilities of a subject during successive tests, the apparatus including:
        a display apparatus configured to provide to the subject a visual contact with a three-dimensional environment, the display apparatus being configured to display stereoscopic images of virtual objects moving in the three-dimensional environment, and
        a response interface; and
    a training sequence controller configured to:
        define a training sequence, the training sequence including a first plurality of successive tests and a second plurality of successive tests, wherein the virtual objects move in a single three-dimensional spatial zone formed by the three-dimensional environment during the first plurality of tests;
        cause the display apparatus to present the first plurality of successive tests to the subject;
        receive, through the response interface, responses from the subject, the responses identifying the virtual objects during the first plurality of successive tests;
        cause the display apparatus to segment the three-dimensional environment into a plurality of three-dimensional spatial zones, wherein the virtual objects move in the plurality of three-dimensional spatial zones during the second plurality of tests;
        cause the display apparatus to present the second plurality of successive tests to the subject;
        receive, through the response interface, responses from the subject, the responses identifying the virtual objects during of the second plurality of successive tests; and
        adjust a speed of the virtual objects in view of the responses received from the subject.

2. A perceptual-cognitive-motor learning system as defined in claim 1, wherein the display apparatus further comprises a positional sensor adapted for detecting an orientation of the subject and for changing the subject's viewing perspective of the three-dimensional spatial zone or zones as a function of the orientation of the subject.

3. A perceptual-cognitive-motor learning system as defined in claim 1, comprising means for using in the spatial zones avatars performing specific and non-specific actions.

4. A perceptual-cognitive-motor learning system as defined in claim 1, wherein the virtual objects perform specific and non-specific actions.

5. A perceptual-cognitive-motor learning system as defined in claim 1, comprising means for introducing a subject's cognitive demand in the spatial zone or zones.

6. A perceptual-cognitive-motor learning system as defined in claim 1, wherein the plurality of spatial zones comprises a segmented scene including a plurality of distinct motion components.

7. A method for evaluating or improving perceptual-cognitive abilities of a subject, comprising:
    displaying stereoscopic images of virtual objects moving in a three-dimensional environment on a display apparatus configured to provide to the subject a visual contact with the three-dimensional environment;
    defining a training sequence, the training sequence including a first plurality of successive tests and a second plurality of successive tests, wherein the virtual objects move in a single spatial zone formed by the environment during the first plurality of tests;

presenting, on the three-dimensional environment, the first plurality of successive tests to the subject;

receiving, through a response interface, responses from the subject, the responses identifying the virtual objects during the first plurality of successive tests segmenting the three-dimensional environment into a plurality of three-dimensional spatial zones, wherein the virtual objects move in the plurality of three-dimensional spatial zones during the second plurality of tests;

presenting, on the three-dimensional environment, the second plurality of successive tests to the subject;

receiving, through the response interface, responses from the subject, the responses identifying the virtual objects during of the second plurality of successive tests; and adjusting a speed of the virtual objects in view of the responses received from the subject.

8. A method as defined in claim 7, comprising detecting an orientation of the subject and changing the subject's viewing perspective of the three-dimensional spatial zone or zones as a function of the orientation of the subject.

9. A method as defined in claim 7, comprising using in the spatial zones avatars performing specific and non-specific actions.

10. A method as defined in claim 7, wherein the virtual objects perform specific and non-specific actions.

11. A method as defined in claim 7, comprising introducing a subject's cognitive demand in the spatial zone or zones.

12. A method as defined in claim 7, comprising receiving from the subject a command to change at least one parameter of the training sequence.

13. A method as defined in claim 7, comprising:
detecting brain waves of the subject; and
changing at least one parameter of the training sequence based on an analysis of the detected brain waves.

* * * * *